US00PP36281P2

(12) United States Plant Patent
Kievit

(10) Patent No.: US PP36,281 P2
(45) Date of Patent: Dec. 3, 2024

(54) ***BRUNNERA* PLANT NAMED 'Balbrufline'**

(50) Latin Name: *Brunnera macrophylla*
Varietal Denomination: Balbrufline

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/371,941

(22) Filed: Sep. 22, 2023

(51) Int. Cl.
*A01H 5/02* (2018.01)
*A01H 6/00* (2018.01)
*A01H 6/12* (2018.01)

(52) U.S. Cl.
USPC ..... Plt./412
CPC ..... *A01H 6/00* (2018.05); *A01H 6/12* (2018.05)

(58) Field of Classification Search
USPC ..... Plt./412
CPC ..... A01H 5/02
See application file for complete search history.

(56) References Cited

PUBLICATIONS https://www.youtube.com/watch?v=kKZxUDzUj4o; Jul. 26, 2023; 1 page.*
https://www.ballseed.com/WEBTRACKPLANTINFO.ASPX?PHID=011600001051625&env=P; May 14, 2024; 2 pages.*
https://www.macore.com/files/2023-2024/2023-2024%20Macore%20Lister%20Herbaceous.pdf; 2023; 2 pages.*
In re Wingen; Feb. 2, 2023; 9 pages.*

* cited by examiner

*Primary Examiner* — Kent L Bell
(74) *Attorney, Agent, or Firm* — Aubrey Charles

(57) ABSTRACT

A new and distinct cultivar of *Brunnera* plant named 'Balbrufline', characterized by its medium blue-colored flowers with a small white "eye", silvery-colored foliage with dark green venation and bright yellow-green colored margins, and moderately vigorous, mounded growth habit, is disclosed.

1 Drawing Sheet

Latin name of genus and species of plant claimed: *Brunnera macrophylla.*

Variety denomination: 'Balbrufline'.

BACKGROUND OF THE INVENTION

The present invention relates to a new and distinct cultivar of *Brunnera* plant botanically known as *Brunnera macrophylla* and hereinafter referred to by the cultivar name 'Balbrufline'.

The new cultivar originated in a controlled breeding program in Hem, The Netherlands during April 2016. The objective of the breeding program was the development of *Brunnera* cultivars having unique foliage coloration.

The new *Brunnera* cultivar is the result of open-pollination. The female (seed) parent of the new cultivar is 'Frostbite', U.S. Plant Pat. No. 35,059, characterized by its light blue and white colored flowers, silvery-colored foliage with dark green venation and margins; and moderately vigorous, compact-mounded growth habit. The male (pollen) parent of the new cultivar is unknown. The new cultivar was selected as a single flowering plant within the progeny of the above stated open-pollination during March 2017 in a controlled environment in Hem, The Netherlands.

Asexual reproduction of the new cultivar by in vitro propagation since March 2017 in Tenjo, Colombia has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbrufline' as a new and distinct cultivar of *Brunnera* plant:

1. Medium blue-colored flowers with a small white "eye";
2. Silvery-colored foliage with dark green venation and bright yellow-green colored margins; and
3. Moderately vigorous, mounded growth habit.

Plants of the new cultivar differ from plants of the female parent primarily in having bright yellow-green foliage margins unlike the dark green foliage margins of the female parent.

Of the many commercially available *Brunnera* cultivars, the most similar in comparison to the new cultivar is 'Frostbite', U.S. Plant Pat. No. 35,059. However, in side-by-side comparison, plants of the new cultivar differ from plants of 'Frostbite' in at least the following characteristics:

1. Plants of the new cultivar have yellow-green colored margins that are different from the dark green colored margins of plants of 'Frostbite'; and
2. Plants of the new cultivar are taller and wider at fall growth maturity than plants of 'Frostbite'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balbrufline'. The plants were approximately seven months old and grown in 3-quart containers for approximately five months in a double polyethylene greenhouse in West Chicago, Illinois.

DETAILED BOTANICAL DESCRIPTION

Figure 1:
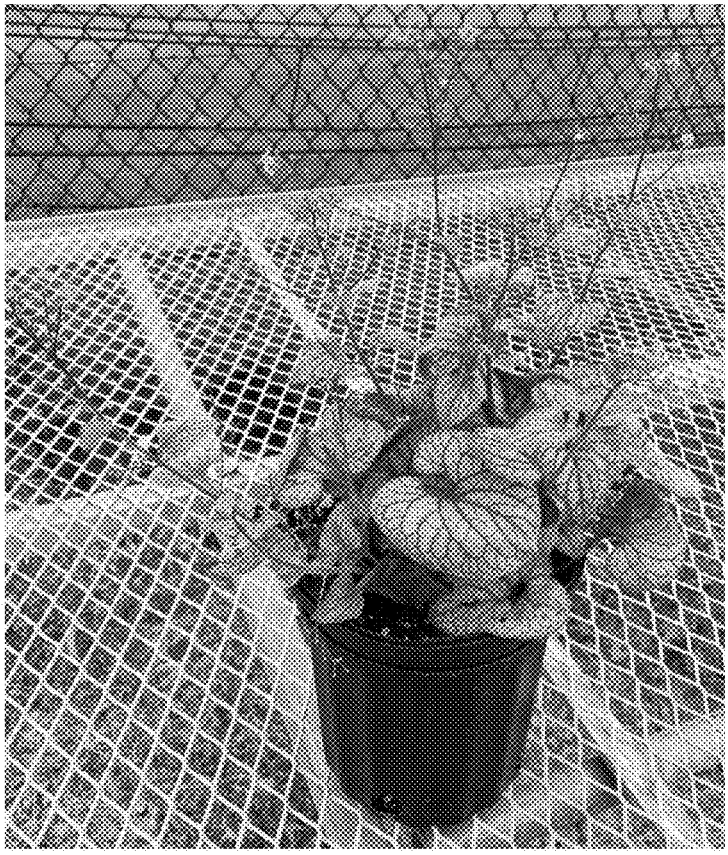
FIG. 1 illustrates a side view of the overall growth habit of 'Balbrufline'.
Figure 2:
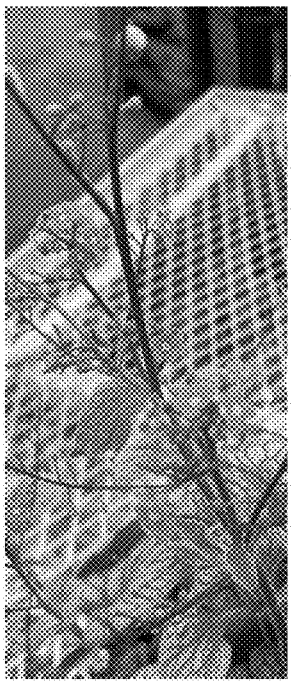
FIG. 2 illustrates a close-up view of an individual inflorescence of 'Balbrufline'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2023 under natural light conditions in Naperville, Illinois.

The following descriptions and measurements describe approximately seven-month-old plants produced from in vitro plantlets and grown under conditions comparable to those used in commercial practice. The plants were grown in 3-quart containers for approximately five months in a double polyethylene greenhouse in West Chicago, Illinois. Greenhouse temperatures were maintained at approximately 51° F. to 56° F. (10.6° C. to 13.3° C.) during the day and approximately 56° F. to 61° F. (13.3° C. to 16.1° C.) during the night. Supplemental lighting was used. Measurements and numerical values represent averages of typical plants.

Botanical classification: *Brunnera macrophylla* 'Balbrufline'.

Parentage:

*Female parent*.—'Frostbite', U.S. Plant Pat. No. 35,059.

*Male parent*.—Unknown.

Propagation:

*Type*.—In vitro propagation is preferred, divisions are possible.

*Time to initiate roots in vitro*.—Approximately 10 days.

*Time to produce a rooted plantlet in summer*.—Approximately 7 to 8 weeks.

*Root description*.—Rhizomatous with fine, fibrous secondary roots.

*Rooting habit*.—Freely branching.

Plant description:

*Commercial crop time*.—Approximately 10 to 12 weeks from a rooted tissue culture plantlet to finish in a 15 cm container.

*Growth habit and general appearance*.—Clump-forming herbaceous perennial, mounded growth habit.

*Growth rate*.—Moderately vigorous.

*Hardiness*.—USDA Zone 4a (−30° F. to −25° F./−34.4° C. to −31.7° C.).

*Size*.—Height from soil level to top of foliage: Approximately 14.0 cm. Width: Approximately 24.0 cm. Reaching up to approximately 30.0 cm in height and approximately 46.0 cm in width in the fall.

*Branching habit*.—No branching, basal rosettes. Number of rosettes per plant: Approximately 6.

Foliage description:

*General description*.—Quantity of leaves per rosette: Approximately 4. Fragrance: None detected. Form: Simple. Arrangement: Basal.

*Leaves*.—Aspect: Blade is at an acute angle to nearly perpendicular to petiole. Shape: Deltoid. Margin: Entire, often with one or two undulations. Apex: Broadly acute. Base: Deeply cordate. Venation pattern: Pinnate. Length of mature leaf: Approximately 8.0 cm. Width of mature leaf: Approximately 7.0 cm. Texture of upper surface: Densely pubescent, setose. Texture of lower surface: Densely pubescent setose on venation. Color of upper surface of young foliage: Closest to 190D with margins of 144A and venation of 138A. Color of lower surface of young and mature foliage: 138B with venation between 138A and 138B. Color of upper surface of mature foliage: Closest to 190D with margins of 144A and venation of 137A.

*Petiole*.—Length: Approximately 7.5 cm. Diameter: Approximately 3.0 mm. Texture: Densely pubescent. Color: 146B with an overlay of N186A. Strength: Moderately strong, flexible.

Flowering description:

*Flowering habit*.—'Balbrufline' requires vernalization for spring flowering. Can flower sporadically during late summer under outdoor conditions.

*Lastingness of individual flower on the plant*.—Approximately 3 to 5 days.

Inflorescence description:

*General description*.—Type: Paniculate cyme emerging from the base of the rosette. Fragrance: None detected. Length: Approximately 30.0 cm. Width: Approximately 6.0 cm. Quantity of inflorescences per plant: Approximately 10. Quantity of flowers per plant: Approximately 25 to 40.

*Peduncle*.—Strength: Moderate. Aspect: Erect to approximately 45° angle from vertical. Length: Approximately 20.0 cm. Diameter at midpoint: Approximately 3.0 mm. Texture: Densely pubescent setose. Color: 146B with an overlay of N186A.

Flower description:

*General description*.—Type: Single, actinomorphic.

*Bud*.—Rate of opening: Generally takes 4 days for bud to progress from first color to fully open flower.

*Bud just before opening*.—Shape: Globose. Diameter: Approximately 2.0 mm. Texture: Moderately pubescent. Color: 146C.

*Corolla*.—Shape: Rotate. Diameter: Approximately 7.0 mm. Depth: Approximately 2.0 mm.

*Petals*.—Quantity: 5. Shape: Obovate. Appearance: Dull. Margin: Entire. Apex: Obtuse. Base: Fused. Length: Approximately 3.0 mm. Width: Approximately 3.0 mm. Texture of upper and lower surfaces: Glabrous. Color of upper surface when first and fully open: 101B with base of NN155D forming a small central floral "eye". Color of lower surface when first and fully open: 97B.

*Calyx*.—Shape: Cup-like. Diameter: Approximately 2.0 mm. Depth: Approximately 1.5 mm.

*Sepals*.—Quantity per flower: 5. Shape: Ovate. Margin: Entire. Apex: Acute. Base: Fused. Length: Approximately 1.5 mm. Width: Approximately 1.0mm. Texture of upper (inner) surface: Glabrous. Texture of lower (outer) surface: Moderately pubescent. Color of upper (inner) surface: 146D. Color of lower (outer) surface: 146D.

*Pedicel*.—Strength: Moderate. Length: Approximately 4.0 mm. Diameter: Approximately 1.0 mm. Texture: Densely pubescent. Color: 146B tinted with 187A.

*Reproductive organs*.—Androecium: Quantity: 5 per flower, adnate to corolla. Anther shape: Winged. Anther length: Less than 1.0 mm. Anther color: 203A. Filament length: Approximately 1.0 mm. Filament color: NN155D. Pollen amount: Abundant. Pollen color: NN155D. Gynoecium: Pistil quantity: 1 per flower. Pistil length: Approximately 1.0 mm. Stigma shape: Rounded. Stigma color: 145D. Style color: 145D. Ovary shape: 4 lobed, deeply divided. Ovary color: N144C.

Seed and fruit production: Neither seed nor fruit production has been observed.

Disease and pest resistance: Resistance to pathogens and pests common to *Brunnera* has not been observed.

What is claimed is:

1. A new and distinct cultivar of *Brunnera* plant named 'Balbrufline', substantially as herein illustrated and described.

* * * * *